United States Patent [19]

Evain et al.

[11] Patent Number: 5,195,120
[45] Date of Patent: Mar. 16, 1993

[54] METHOD, TUBE AND SYSTEM FOR ELIMINATING A FIXED ANTISCATTER GRID IN A RADIOLOGICAL IMAGE

[75] Inventors: Bernard Evain, Issy les Moulineaux; Olivier Peyret, Grenoble; Horia Dumitrescu, Guyancourt, all of France

[73] Assignee: General Electric CGR S.A., Issy les Moulineaux, France

[21] Appl. No.: 811,649

[22] Filed: Dec. 23, 1991

[30] Foreign Application Priority Data

Dec. 28, 1990 [FR] France .................. 90 16464

[51] Int. Cl.$^5$ ............................. G21K 1/00
[52] U.S. Cl. ......................... 378/154; 378/62
[58] Field of Search ........................ 378/154, 62

[56] References Cited

U.S. PATENT DOCUMENTS

4,380,086  4/1983  Vagi .
5,050,198  9/1991  Honda .................. 378/154

FOREIGN PATENT DOCUMENTS

182637  5/1986  European Pat. Off. .

*Primary Examiner*—Craig E. Church
*Attorney, Agent, or Firm*—Pollock, VandeSande & Priddy

[57] ABSTRACT

In a radiological apparatus using an antiscatter grid, this grid is kept fixed instead of being movable, and its image is removed by irradiating it as well as the object to be examined by two X-ray sources that have to be separated by a distance b determined by the first zero of the modulation transfer function of this two-source system. To take account of the magnification G, the distance b can be adjusted by means of a cathode emitting two electron beams with adjustable deflection.

2 Claims, 5 Drawing Sheets

METHOD, TUBE AND SYSTEM FOR ELIMINATING A FIXED ANTISCATTER GRID IN A RADIOLOGICAL IMAGE

BACKGROUND OF THE INVENTION

The invention generally relates to radiological devices that create the image of an object through the use of an X-radiation that irradiates the object. It relates, more particularly, to a method, an X-ray tube and a system for the elimination, from the image of the object, of the image corresponding to a fixed antiscatter grid.

Figures 1, 2:
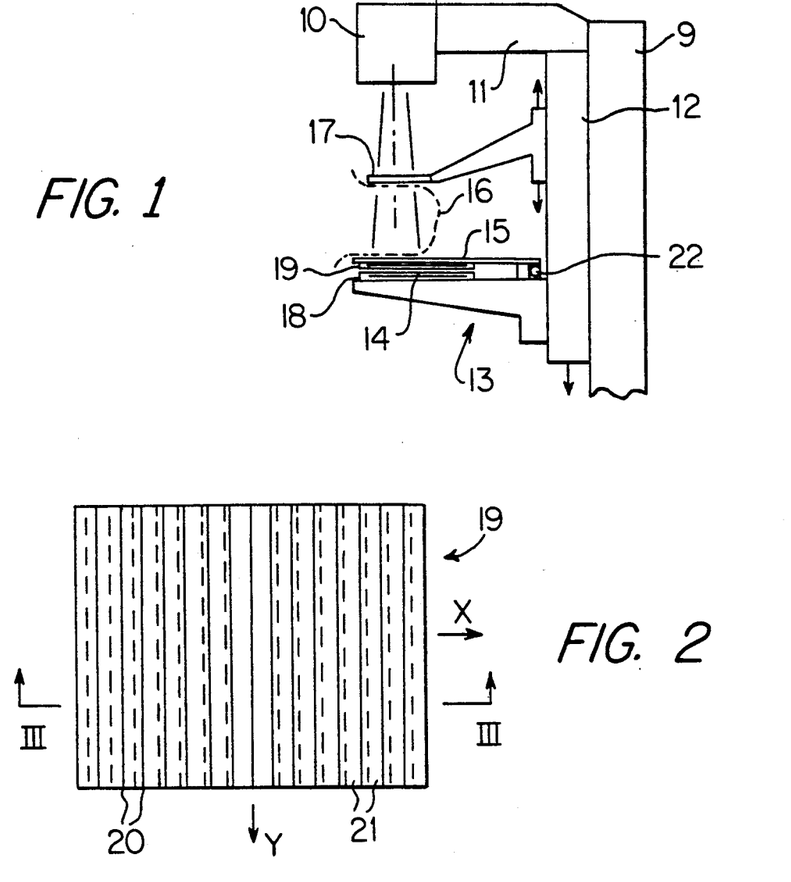
FIG. 1 shows a schematic sectional view of a mammograph to which the invention can be applied more particularly.
FIG. 2 shows a top view of an antiscatter grid used in a mammograph.

The invention shall be described in its implementation into a mammography apparatus of the type shown schematically in FIG. 1.

This mammography apparatus has an X-radiation source 10 borne by a bracket 11 positioned at the top of a vertical plate 12. This vertical plate 13 has an assembly 13 on which there lies a breast 16 to be examined by means of a horizontal shelf 15 as a support. A pad 17, that is transparent to X-radiation and is vertically movable, is used to compress the breast.

To match the size of the breast, the plate 12 is mounted on a vertical column 9 resting on the ground, and shifts vertically on said column by means of an appropriate mechanical device.

On its upper part and beneath the shelf 15, the assembly 13 has a tunnel in which there is housed a cartridge 18 constituted by a black box enclosing a film 14 sensitive to direct X-radiation or to a photon radiation emitted by a screen (not shown) that receives the X-radiation. It is on this film 14 that there is formed the latent image of the breast after an appropriate exposure time. The development of the film gives a radiographic picture.

In a mammograph, the breast 16 under examination is close to the radiographic film 14, and as a result of scattering by the different points of the breast, the contrast and resolution of the image are diminished. To prevent this phenomenon, a grid 19, known as an antiscatter grid, is interposed between the breast and the radiological film. This grid 19 eliminates all the scattered rays having an angle of incidence on the film 14 that is greater than a certain value.

A grid such as this (FIGS. 2 and 3) has a succession of lead strips 20, lead being a material that absorbs X-radiation, separated by interposed elements 21 made of a material that absorbs little X-radiation, for example, a material such as paper or aluminium. These strips are oriented convergently towards the focal spot of the X-ray tube. Typically, the strips have a thickness d=10 to 30 microns for a pitch of D=100 to 300 microns and a height h of a few millimeters.

Figure 3:
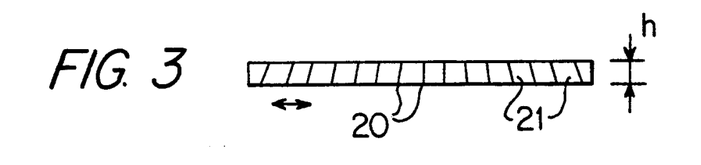
FIG. 3 shows a sectional view of an antiscatter grid along the line III—III of FIG. 2.

Since a grid such as this has strips that are opaque to X-radiation, each of these strips gives an image on the radiological film. Hence, to eliminate this image of the grid, there is a known way of communicating an alternating motion of a few hertz to the grid to make it invisible on the radiological image. This alternating motion is generally obtained by a motor 22, which increases the space occupied by the unit.

SUMMARY OF THE INVENTION

An object of the present invention is therefore to implement a method that enables the use of a fixed grid and the elimination of the image of the grid from the radiological film.

In this method, the object is irradiated by two simultaneous X-ray beams obtained by means of an X-ray tube with two focal spots of identical width, spaced out by a distance b that is chosen so as to obtain the elimination of the image of the grid.

The distance b is determined through the computation of the modulation transfer function of an X-ray tube with two focal spots.

More precisely, in a radiological apparatus comprising at least one X-ray source irradiating an object to be examined that is located at a distance c from said source, and an antiscatter grid with a spatial frequency $F_g$ placed between said object and a receiver located at a distance d from said object, the invention relates to a method enabling the elimination of the image of said antiscatter grid that consists in:

keeping the antiscatter grid fixed, simultaneously irradiating said object by a second source of X-rays having a spatial energy distribution that is substantially identical to that of the first source, and choosing the distance b between the two X-ray sources so that:

$$b = \frac{G}{G-1} \cdot \frac{1}{2F_g} \quad (1)$$

with a magnification $$G = \frac{c+d}{c}$$

Should the magnification G vary, it is further necessary to modify the distance b.

The two sources of X-radiation are formed by means of an X-ray tube comprising a cathode with two filaments, each filament being associated with a focusing and deflection device, the mechanical and electrical characteristics as well as the applied voltages of which are such that it gives rise, at an anode positioned so as to face said cathode, to two X-ray sources separated by a distance b, the two X-ray sources thus obtained having a spatial energy distribution that is as identical as possible.

The two filaments of the cathode may be identical or not identical but, in both cases, calibrations of the X-ray tube make it possible to determine the voltages to be applied to the focusing and deflection devices to obtain, for both focal spots, the same width a and spacing b as a function of the enlargement G.

BRIEF DESCRIPTION OF THE DRAWINGS

Other objects, advantages and features of the present invention shall appear from the following description of a particular exemplary embodiment, said description being made with reference to the appended drawings, of which.

MORE DETAILED DESCRIPTION

In order to eliminate the image of an antiscatter grid with a spatial frequency $F_g$ on a radiological film, the invention proposes the use of an X-ray tube having two focal spots with a width a and a spacing b such that the modulation transfer function has a cut-off frequency for the spatial frequency $F_g$. The way in which an elimination such as this is obtained shall be explained by means of the graphs of FIGS. 4 to 9.

Figure 4:
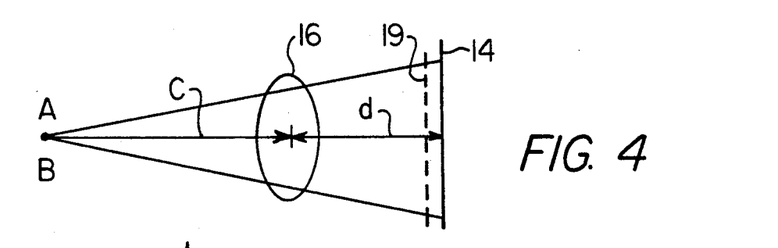
FIG. 4 is a diagram showing the respective positions of the focal spot, the object, the antiscatter grid and the radiological film in a radiological apparatus.

The diagram of FIG. 4 indicates the respective positions of the focal spots A and B of an object to be examined such as the breast 16, of the antiscatter grid 19 and of a receiver such as the radiological film 14. If c is the distance between the focal spots and the breast 16, and d is the distance between the breast 16 and the film 14, a magnification G is defined as the ratio:

$$G = \frac{c + d}{c}$$

Figure 5:
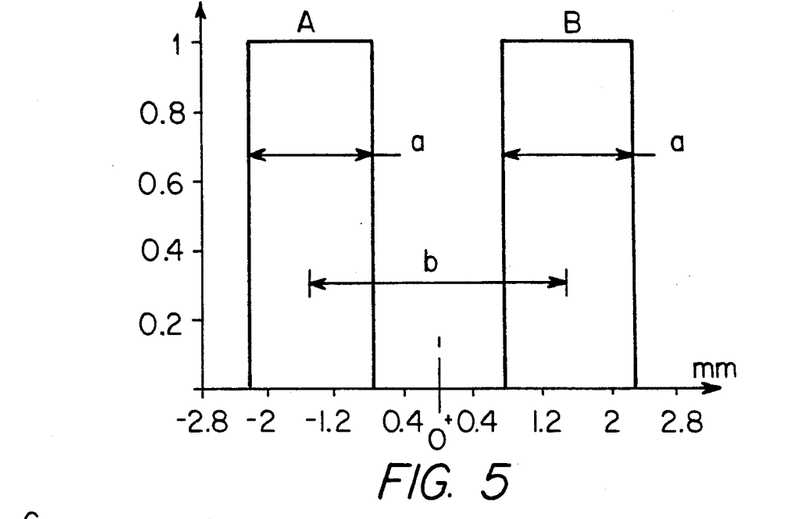
FIG. 5 is a graph showing the theoretical energy distribution of two neighboring focal spots and their respective positions.

FIG. 5 shows the theoretical energy distribution of the focal spots A and B as a function of their x-axis value with respect to a midpoint 0. For each focal spot, this distribution has a rectangular shape that is assumed to be perfect.

Figure 6:
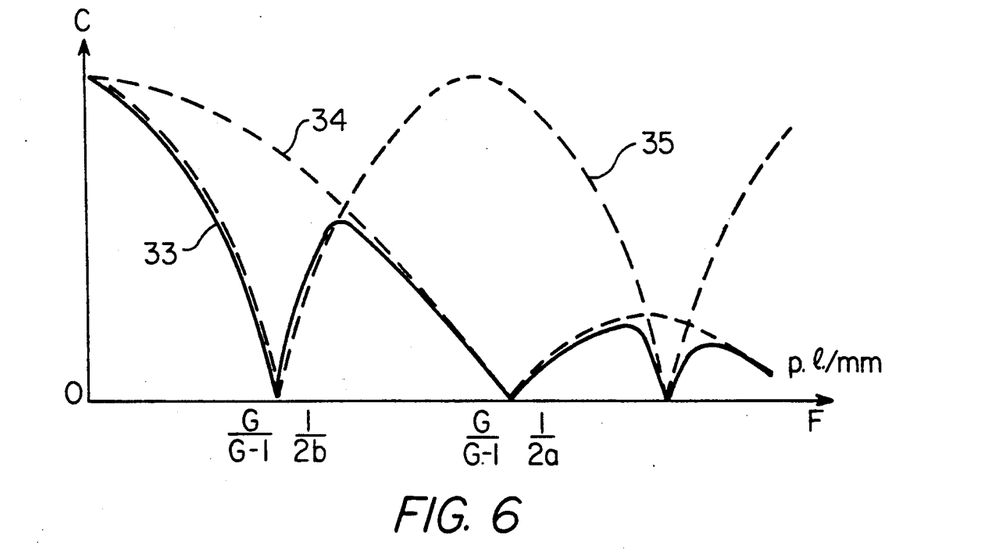
FIG. 6 is a graph that can be used to determine the modulation transfer function curve of an X-ray emitter comprising two identical focal spots.

The modulation transfer function of the two focal spots A and B presenting the energy distribution of the graph of FIG. 5, which is given by the modulus of the optical transfer function, is represented by the solid line curve 33 of FIG. 6. In this FIG. 6, the y-axis is graduated in contrast values from 0 to 1 defined as the ratio C such that:

$$C = \frac{Imax - Imin}{Imax + Imin}$$

$I_{max}$ being the maximum value and $I_{min}$ being the minimum value of the luminous intensity.

The x-axis is graduated in spectral frequency F and, more precisely, in pairs of lines per millimeter which, for an antiscatter grid, signifies the number of pairs of X-ray opaque strips per millimeter (p.l./mm).

This curve 33 is the product of the two curves 34 and 35 shown in dashes. The curve 34 is of the type modulus of:

$$\frac{\sin x}{x}$$

and depends only on the width a of the focal spots A and B. The curve 35 is of the type modulus of (cos y) and depends only on the spacing b of the focal spots A and B.

Given that b is generally greater than a, the first value of the spatial frequency for which the contrast is cancelled out is given by:

$$\frac{G}{G-1} \cdot \frac{1}{2b}$$

i.e. by the $|\cos y|$ type curve.

As a rule, the spatial frequencies for which $|\cos y| = 0$ are given by:

$$F_{oy} = (2k + 1) \cdot \frac{G}{G-1} \cdot \frac{1}{2 F_g} \text{ with } k \geq 0 \quad (4)$$

The second value of the spatial frequency for which the contrast gets cancelled out is given by $$\frac{G}{G-1} \cdot \frac{1}{a} \quad (5)$$

i.e. by a curve of the $$\left| \frac{\sin x}{x} \right|$$

type when $b < 3a$.

As a rule, the spatial frequencies for which $$\left| \frac{\sin x}{x} \right|$$

are given by:

$$F_{ox} = 2k \cdot \frac{G}{G-1} \cdot \frac{1}{2a} \text{ with } k \geq 1 \quad (6)$$

The resultant curve 33, which is the product of the curves 34 and 35, shows that to eliminate an object having a spatial frequency $F_g$ from the image, it is necessary to choose, for a given magnification G, a value of the spacing b such that:

$$F_g = \frac{G}{G-1} \cdot \frac{1}{2b} \quad (7)$$

giving $$b = \frac{G}{G-1} \cdot \frac{1}{2F_g} \quad (1)$$

Figure 7:
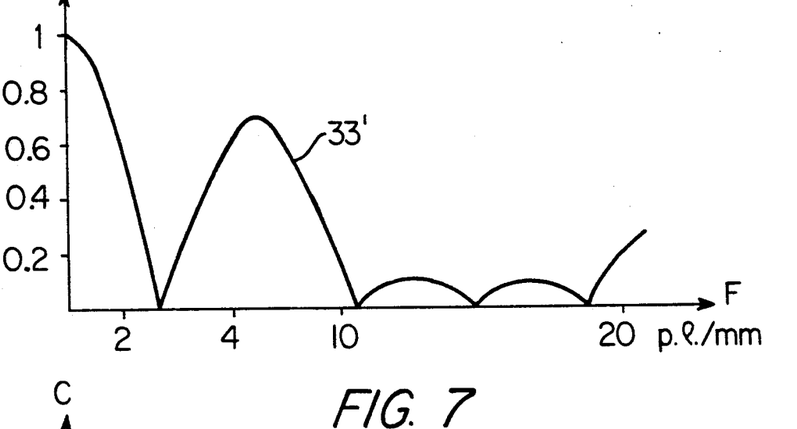
FIG. 7 is a graph similar to that of FIG. 6, but with a graduated x-axis.
Figure 8:
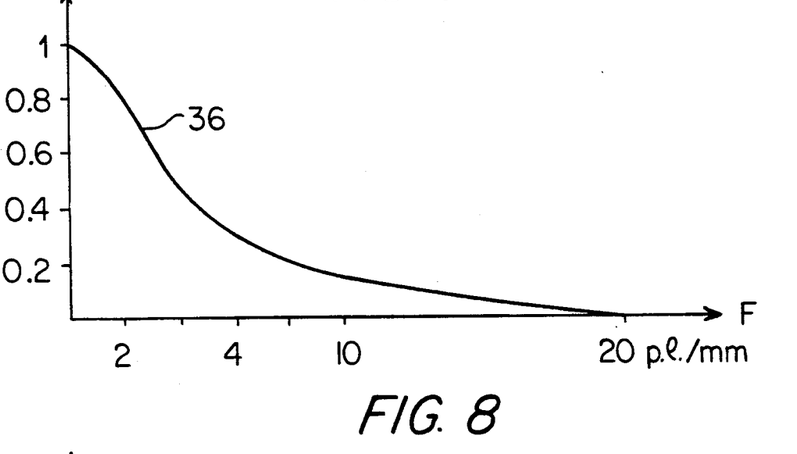
FIG. 8 is a graph giving the curve of the modulation transfer function of an X-ray receiver such as a radiological film.

The modulation transfer function of the focal spots A and B as represented by the curve 33 of FIG. 6 or the curve 33' of FIG. 7 does not take account of the modulation transfer function of the receiver represented by the curve 36 of FIG. 8. If this function is taken into account, the modulation transfer function of the image system is represented by the curve 37 of FIG. 9 which is the product of the curves 33' and 36.

Figure 9:
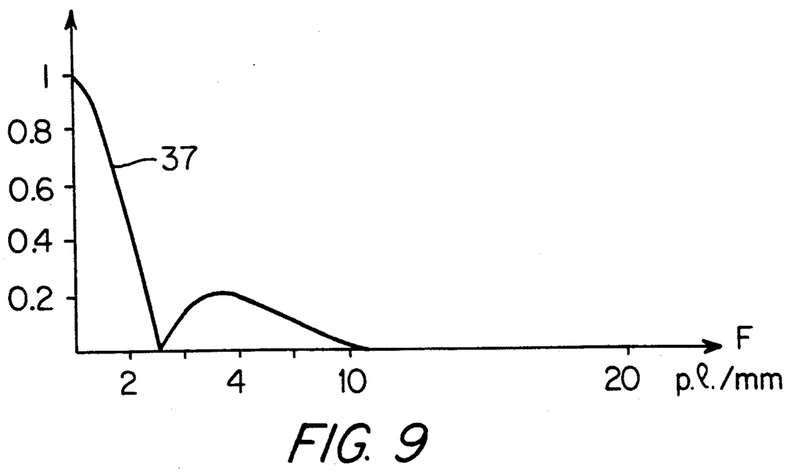
FIG. 9 is a graph giving the curve of the modulation transfer function of an image system comprising an emitter with two focal spots and a receiver.

The curve 33' of FIG. 7 is similar to the curve 33 of FIG. 6, but its x-axis has been plotted to the same scale as in FIGS. 8 and 9. The X-ray tubes, which have two focal spots, are known, but the characteristics of each of the focal spots are generally different for it is desired to obtain X-rays having different characteristics.

To make an X-ray tube having two simultaneous focal spots, it is necessary to use two electron transmission sources, i.e. two emitting filaments. This may be obtained in different ways, for example, by two separate cathodes each having an emitting filament.

According to the invention, it is preferable to use only one cathode having two filaments. Three exemplary embodiments of a cathode such as this shall be described with reference to FIGS. 10, 11 and 12.

Figure 10:
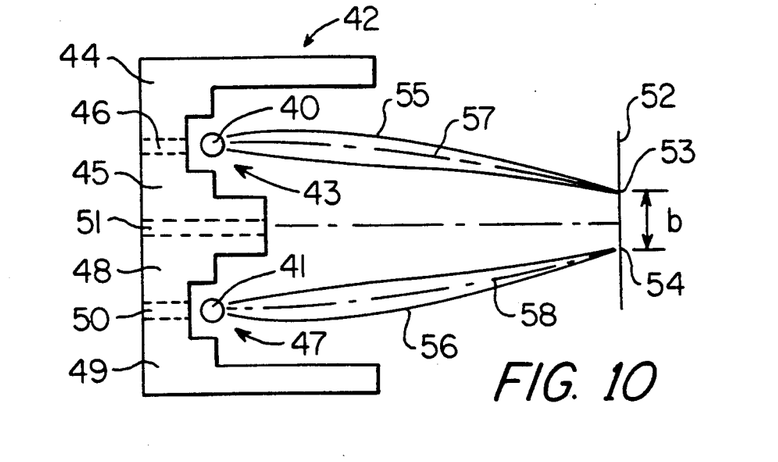
FIGS. 10, 11 and 12 are drawings of a cathode of an X-ray tube that can be used to obtain two identical focal spots, the spacing of which can be variable.

In the exemplary embodiment of FIG. 10, a cathode 42 has two identical filaments 40 and 41 that are positioned in a concentration element, divided into two identical parts, one to focus the electrons emitted by the filament 40 and the other to focus the electrons emitted by the filament 41.

It is thus that the filament 40 is positioned at the bottom of a stepped groove 43 made of two metal parts 44 and 45 attached to each other but insulated from each other by an insulating layer or partition 46.

In the same way, the filament 41 is located at the bottom of a stepped groove 47 that is made of two metal parts 48 and 49 that are attached to but insulated from each other by an insulating layer 50. The central metal parts 45 and 48 are attached to but insulated from each other by an insulating layer 51. The concentration element thus has four metal parts 44, 45, 48 and 49 that are attached to but insulated from one another. This arrangement enables the application of different voltages to the different metal parts and hence the modification of the focusing of the electron beams 55 and 56, i.e. the dimensions of their point of impact 53 and 54 on the anode 52 and notably the dimension a. Furthermore, it also enables the modification of the angular position of the axis of emission 57 and 58 of said beams to modify the distance b between the points of impact 53 and 54 corresponding to the two focal spots.

While the cathode described with reference to FIG. 10 is satisfactory for the implementation of the invention, it is not sophisticated enough to fulfil certain other functions implemented in radiological instruments, such as obtaining X-rays with different characteristics. To this effect, there is a known method of using cathodes comprising two cathodes that have different characteristics and are used successively, i.e. non-simultaneously. In order to continue to fulfil the requisite functions while at the same time implementing the present invention, these cathodes have to be modified, and FIGS. 11 and 12 show examples of such modifications, resulting from the exemplary embodiment described with reference to FIG. 10.

Figure 11:
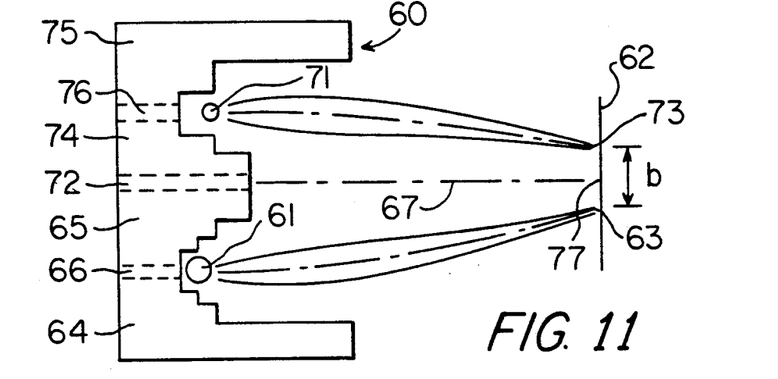
Figure 12:
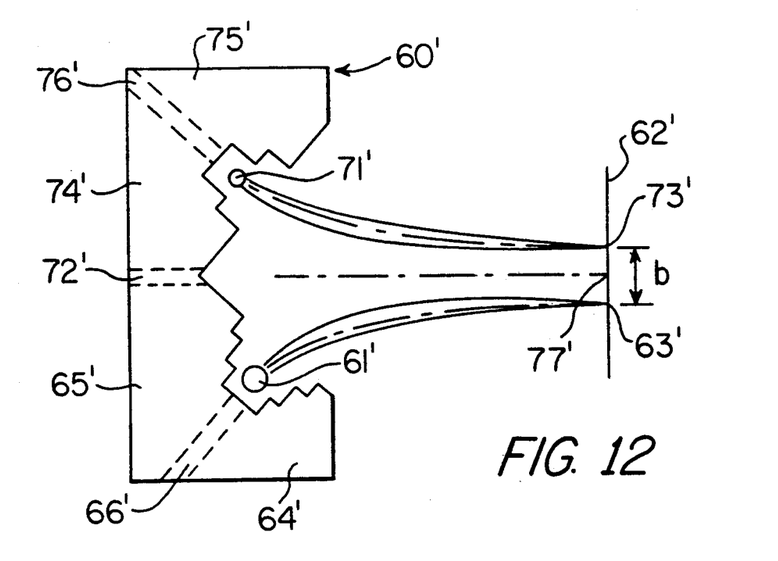

In FIG. 11, a cathode 60 has a first filament 61, the dimensions of which are such that it gives rise, at an anode 62, to a first focal spot 63 known as the "large focal spot". The electrons emitted by the first filament 61 are focused and sent towards the focal spot 63 by a first focusing device that has two metal parts 64 and 65, which are attached to but insulated from each other by an insulating layer 66. These two parts 64 and 65 form, around the filament 61, a concentration element with a well-known three-stepped shape.

The cathode 60 has a second filament 71, the dimensions of which are smaller than those of the first filament 61. This second filament 71 gives rise, at the anode 62, to a second focal spot 73 called a "small focal spot". The electrons emitted by this second filament 71 are focused and directed towards the focal spot 73 by a second focusing device that has two metal parts 74 and 75 which are attached to but insulated from each other by an insulating layer 76. These two metal parts 74 and 75 form, around the filament 71, a concentration element with a two-stepped shape.

The two focusing devices are attached by the metal parts 65 and 64 which are insulated from each other by an insulating layer 72.

The number of steps of each focusing device as well as the height of said steps are different in order to obtain the desired focusing and deflection of the electron beams, the intensity of which is generally different for the characteristics of the filaments (dimensions, lengths, resistance values, heating currents. The mechanical characteristics of the focusing devices are generally not sufficient to obtain the desired effects: there is therefore provision for the application of the different voltages to the metal parts 64, 65, 74 and 75, and this is the reason for their electrical insulation with respect to one another. The making of a cathode such as this is within the scope of those skilled in the art.

The exemplary embodiment of FIG. 12 is similar to that of FIG. 11 with the difference that the axes of the focusing devices are not parallel to one another as in FIG. 11 but are secant, and what is called a dihedron-shaped cathode is obtained. In this FIG. 12, the elements similar to those of FIG. 11 bear the same references but have the added sign "'".

In the X-ray tubes with two focal spots used in standard type radiological devices, only one focal spot is used at a time and it is enough to focus one of the two electron beams at a point 77 that will be the same for the two beams.

To use an X-ray tube such as this in order to implement the present invention, it is necessary to simultaneously obtain two focal spots 63 and 73 that are as identical as possible and are separated by a determined distance b.

To this effect, the mechanical and electrical characteristics of the focusing devices of each element as well as the values of the heating currents of said filaments are determined to enable the modification of the focusing of the beams so that they give rise to identical focal spots and to the modification of their deflection in order to obtain the distance b between the focal spots.

It is important to be able to modify the distance in order to take account of the fact that the magnification G of the radiological apparatus changes according to the type of exposure.

To determine the potentials to be applied to the metal parts of the different focusing and deflection elements of the cathodes of FIGS. 10, 11 and 12, it is necessary to carry out calibrations of the X-ray tube comprising said cathode by varying the voltages U applied to the different metal parts. These calibrations have also been described in the corresponding U.S. patent application Ser. No. 07/649,041 filed on Feb. 1st, 1991, but shall be described again herein in their application to the cathode 60 of FIG. 11.

Figure 13A:
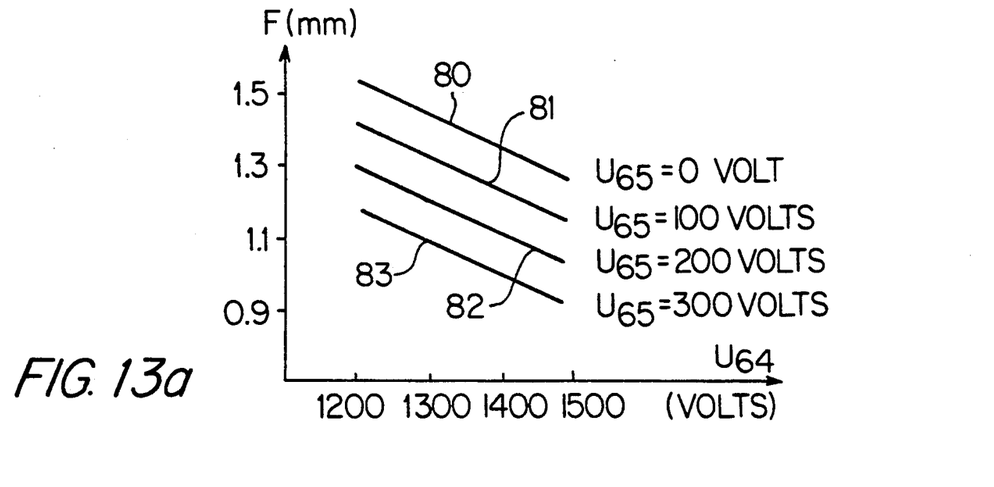
FIGS. 13a, 13b and 13c are graphs that make it possible to determine the voltages to be applied to the focusing and deflection electrodes, to obtain focal spots having desired characteristics.

A first calibration consists in measuring the width f of the point of impact of the electron beam on the anode 62, i.e. the width of the focal spot of the X-ray beam as a function of the potential $U_{64}$ applied to the part 64 for different values of $U_{65}$ applied to the part 65. The curves 80 to 83 of FIG. 13a are obtained. These curves 80 to 83 correspond respectively to $U_{65}=0$ volts, $-100$ volts, $-200$ volts and $-300$ volts.

Figure 13B:
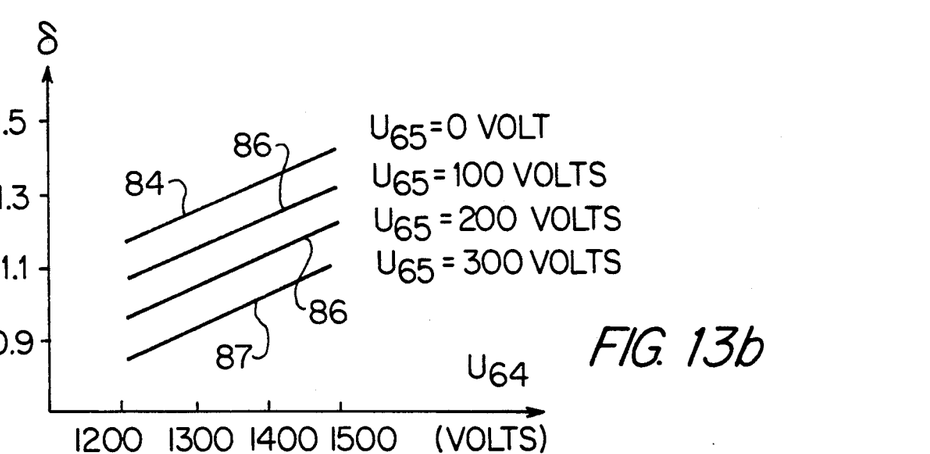

A second calibration consists in measuring the deflection $\delta$ of the electron beam, namely the shifting of its focal spot 62 on the anode 63 with respect to a median axis or plane 67 as a function of the potential $U_{64}$ and for the same values of $U_{65}$. The curves 84 to 87 of FIG. 13b are obtained. These curves 80 to 83 correspond respectively to $U_{65}$ 0 volts, $-100$ volts, $-200$ volts and $-300$ volts.

Figure 13C:
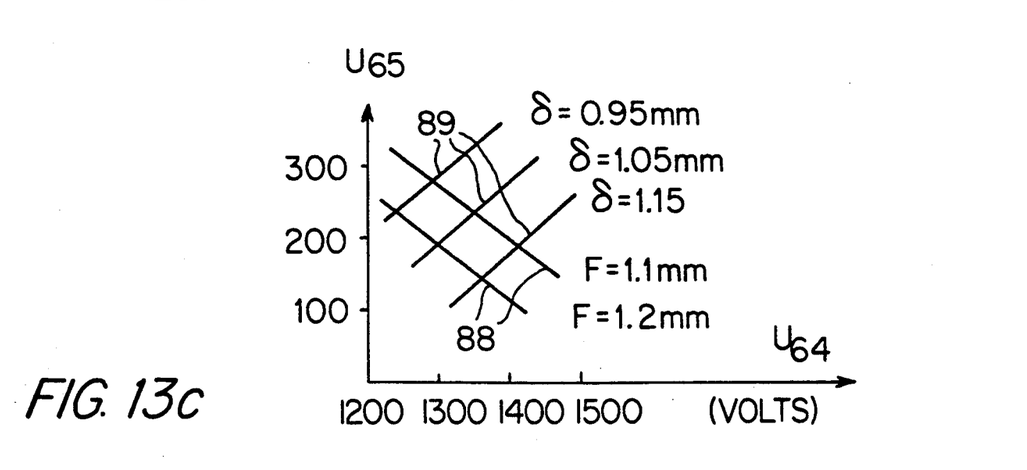

The combination of the curves of FIGS. 13a and 13b makes it possible to obtain the two systems of curves of FIG. 13c, i.e. to obtain $U_{65}$ as a function of $U_{64}$ for different values of the width f of the point of impact (network 88) and for different values of the deflection $\delta$ of the beam (network 89). In this FIG. 13c, the coordinates of the points of intersection of the curves of the two networks 88 and 89 give the values of $U_{64}$ and $U_{65}$ to obtain the width of the focal spot and of its deflection as indicated by the secant curves.

Naturally, these calibrations described here above also have to be performed for the beam controlled by the parts 74 and 75.

In brief, for a given antiscatter grid, i.e. for a given spatial frequency $F_g$, the formula (1) makes it possible to determine the distances b to be set up between the two focal spots for different values of the magnification G which usually varies between 1.05 and 1.2 for, beyond this value, the scattered radiation is eliminated as a result of the path in the air so that the antiscatter grid is no longer used.

Then, the curves of FIG. 13c make it possible to determine the potentials to be applied to the different parts of the focusing and deflection devices to obtain, firstly, each spacing $b=2\delta$ between the focal spots 63 and 73, giving a deflection of b/2 per device and, secondly, the same width a=f per focal spot.

Furthermore, the characteristics of each filament make it possible to determine the heating current to obtain the same energy per focal spot if different filaments are used.

For a given radiological apparatus, these different elements of information are, for example, recorded in the memory of a microprocessor which, for a certain value of magnification, gives the values of the potentials to be applied to the different metal parts of the cathode as well as the values of the heating currents of the filaments in order to obtain the two focal spots with a width a spaced out by the distance b.

Figure 14:
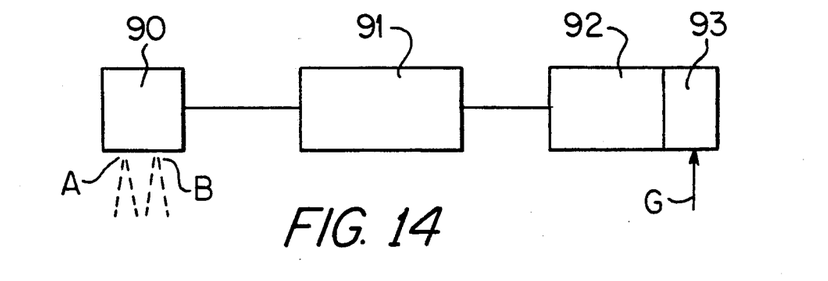
FIG. 14 is a simplified functional diagram of a system according to the invention.

Hence, as shown in FIG. 14, the system, according to the invention, for the elimination of the image of the antiscatter grid, comprises an X-ray tube 90 with two focal spots A and B, the cathode of which has two identical or non-identical filaments that are each associated with a focusing and deflection device. The different supply and biasing voltages of this tube 90 are given by a device 91 which is under the control of a microprocessor 92. This microprocessor has at least one memory 93 which contains the values of the voltages to be applied to the tube 90 as well as the heating currents for the filaments in order to simultaneously obtain two identical focal spots with a width a and a spacing b that enable the elimination of the image of the fixed antiscatter grid for a given magnification G.

To obtain the deflections required of the electron beams, exemplary embodiments have been described wherein the deflections are obtained by the application of the bias voltages to the different parts of the focusing elements. These deflections can also be obtained by other devices such as, for example, additional electrodes which would be placed on either side of each beam and would be electrically insulated from the focusing elements. These devices would be borne by said focusing elements and would constitute extensions of the steps. The use of such additional electrodes would enable the two functions to be separated into two, one being a focusing function reserved for the focusing elements in the vicinity of the filaments and the other being a deflection function reserved for these additional electrodes placed along the beams.

What is claimed is:

1. In a radiological apparatus comprising at least one X-ray source irradiating an object to be examined that is located at a distance c from said source, and an antiscatter grid with a spatial frequency $F_g$ placed between said object and a receiver located at a distance d from said object, a method enabling the elimination of the image of said antiscatter grid that consists in:

keeping the antiscatter grid fixed, simultaneously irradiating said object by a second source of X-rays having a spatial energy distribution that is substantially identical to that of the first source, and choosing the distance b between the two X-ray sources so that:

$$b = \frac{G}{G-1} \cdot \frac{1}{2F_g} \quad (1)$$

with a magnification $$G = \frac{c+d}{c} \quad (2)$$

2. A method according to claim 1 further consisting in:

modifying the distance b between the two X-ray sources when the magnification G varies so as to always have the equality given by:

$$b = \frac{G}{G-1} \cdot \frac{1}{2F_g} \quad (1)$$

* * * * *

UNITED STATES PATENT AND TRADEMARK OFFICE
CERTIFICATE OF CORRECTION

PATENT NO. : 5,195,120
DATED : March 16, 1993
INVENTOR(S) : Bernard Evain, et al It is certified that error appears in the above-identified patent and that said Letters Patent is hereby corrected as shown below:

Column 4, line 41, after the equation insert -- = 0 --.

Column 6, line 22, after "currents" insert -- ) --.

Column 7, line 15, change "$U_{65}0$" to -- $U_{65} = 0$ --.

Signed and Sealed this

Thirtieth Day of November, 1993

Attest:

BRUCE LEHMAN

*Attesting Officer*  *Commissioner of Patents and Trademarks*